US00PP30849P3

(12) United States Plant Patent
Cerny et al.

(10) Patent No.: US PP30,849 P3
(45) Date of Patent: Aug. 27, 2019

(54) APPLE TREE NAMED 'UEB 42723'

(50) Latin Name: ***Malus domestica* (Borkh.)**
Varietal Denomination: UEB 42723

(71) Applicant: Institute of Experimental Botany AS CR, v.v.i. (UEB), Prague (CZ)

(72) Inventors: Radek Cerny, Ricany u Prahy (CZ); Jan Zima, Turnov (CZ); Otto Louda, Pencin u Liberce (CZ); Jaroslav Tupy, Prague (CZ)

(73) Assignee: Institute of Experimental Botany AS CR, v.v.i. (UEB), Prague (CZ)

( * ) Notice: Subject to any disclaimer, the term of this patent is extended or adjusted under 35 U.S.C. 154(b) by 0 days.

(21) Appl. No.: 15/932,513

(22) Filed: Mar. 8, 2018

(65) Prior Publication Data

US 2018/0263157 P1 Sep. 13, 2018

Related U.S. Application Data

(60) Provisional application No. 62/600,978, filed on Mar. 8, 2017.

(51) Int. Cl.
*A01H 5/00* (2018.01)
*A01H 6/74* (2018.01)

(52) U.S. Cl.
USPC ..... Plt./175
CPC ..... *A01H 6/7418* (2018.05)

(58) Field of Classification Search
USPC ..... Plt./156, 175
See application file for complete search history.

*Primary Examiner* — Susan McCormick Ewoldt
(74) *Attorney, Agent, or Firm* — The Webb Law Firm

(57) ABSTRACT

A new and distinct *Malus domestica* (Borkh.) ornamental variety that exhibits a columnar tree growth type, compact growth habit, $V_f$-resistance against scab, attractive red-purple flowers, greyed-purple young leaves, green mature leaves, and small, red colored, obloid shaped fruits that persist on the tree after the fall of leaves into Winter. The new variety is suitable for home apple growing as solitary trees and can be useful for pollinating purposes.

10 Drawing Sheets

Botanical classification: *Malus domestica* (Borkh.).
Varietal denomination: 'UEB 42723'.

BACKGROUND OF THE INVENTION

The present invention comprises a new and distinct cultivar of apple tree botanically classified as *Malus domestica* (Borkh.) and known by the varietal name 'UEB 42723'.

The new variety is the result of a cross in a planned breeding program between 'Evereste' (female parent, unpatented) and 'Maypole' (male parent, U.S. Plant Pat. No. 6,184). The cross resulting in 'UEB 42723' occurred in the Spring of 2003 at 310 meters above sea level with a mean annual temperature of 7.7° C. and a mean annual precipitation of 680 mm. The purpose of the breeding program was to develop an ornamental apple variety having a unique appearance with a columnar tree growth type that exhibits $V_f$-resistance against scab. The new variety was discovered in 2009 with the first flowering and fruiting of the original seedling in the Czech Republic. Subsequently, the new variety was asexually reproduced in Pencin u Liberce in the Czech Republic by budding/grafting on apple rootstocks in the Spring of 2014.

The new variety is similar to its female parent, 'Evereste', in exhibiting small fruits with no russeting present and $V_f$-resistance against scab. However, 'UEB 42723' exhibits a columnar tree growth type, red-purple flower petals, and red fruit skin color, while 'Evereste' exhibits a ramified tree growth type, white flower petals, and yellow fruit skin color with an orange to red blush present. The new variety is similar to its male parent, 'Maypole', in exhibiting a columnar tree growth type, red-purple flower petals, and long fruit stalk. However, 'UEB 42723' exhibits longer persisting fruits than 'Maypole' that are ovoid in shape and leaves that are ovate in shape with a serrate margin, while the fruits of 'Maypole' are round-conical in shape and its leaves are elongated in shape with a crenate margin.

Further, when compared to apple tree named 'UEB 42721' (U.S. Plant patent application Ser. No. 15/932,511, concurrently applied-for herewith), both varieties exhibit a columnar tree growth type and $V_f$-resistance against scab. However, 'UEB 42723' exhibits a compact growth habit and an ovoid fruit shape, while 'UEB 42721' exhibits a more erect growth habit and a broadly globose fruit shape.

The following characteristics also distinguish the new variety from other varieties known to the breeders:

- Late ripening, ornamental, diploid variety;
- Columnar tree growth type;
- Compact growth habit with short internodes;
- Weak to medium tree vigor;
- Red-purple colored flowers;
- Early to medium time to beginning of flowering;
- Greyed-purple color of young leaves and green tinted color of mature leaves;
- Fruit is small in size and ovoid in shape with slight ribbing;
- Long time of fruit persistence; and
- Resistance against scab on $V_f$-gene basis.

The new variety has been trial and field tested and has been found to retain its distinctive characteristics and remain true to type through successive asexual propagations.

DESCRIPTION OF THE DRAWINGS

The accompanying photographic drawings illustrate the new cultivar taken at varying ages of maturity as recited further below, with the color being as nearly true as possible with color illustrations of this type. It should be noted that colors may vary with growing conditions and time of year.

DESCRIPTION OF THE PLANT

Figure 1:
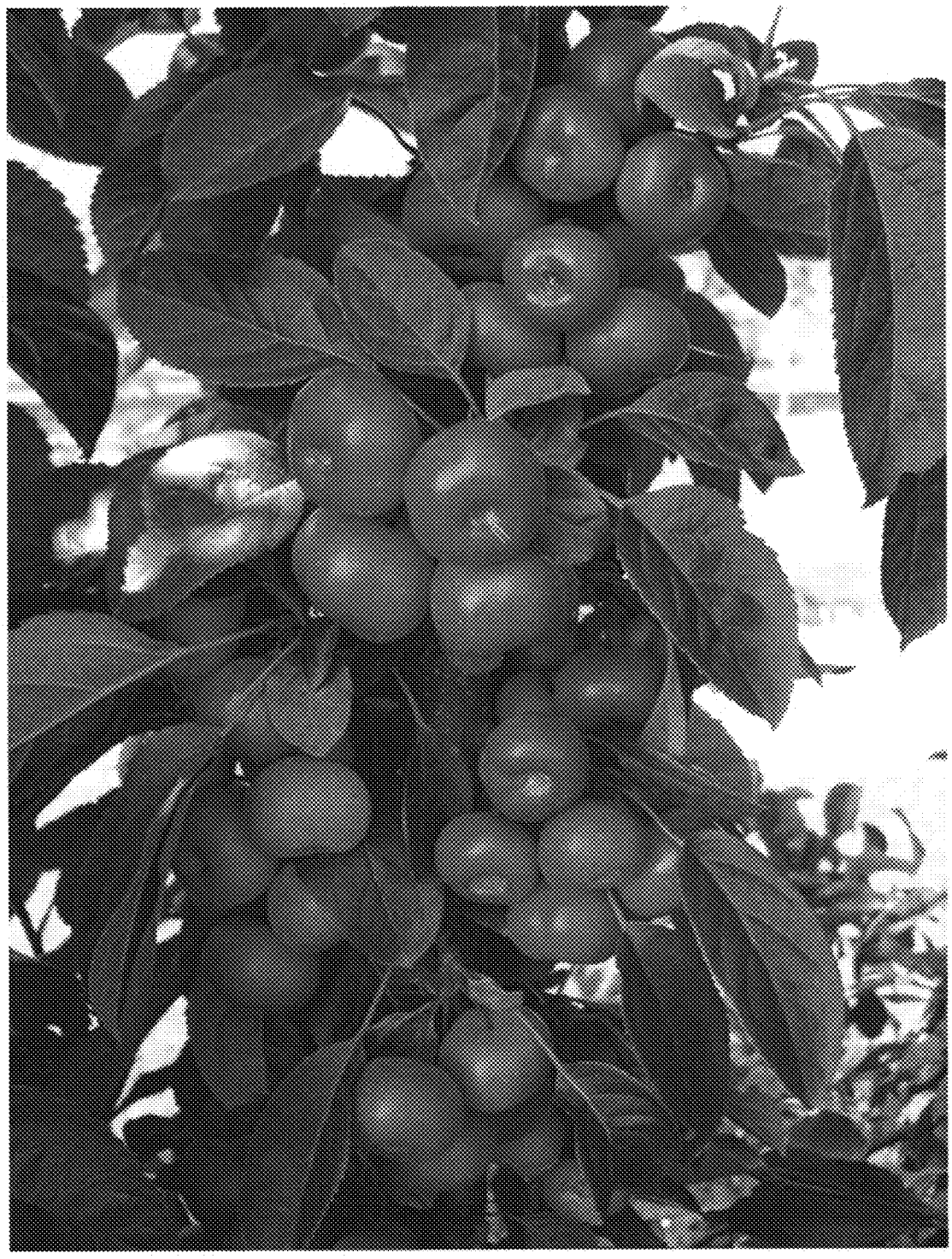
FIG. 1 illustrates a section of the vertical trunk of the new variety at 2 years of age, showing details of its ornamental fruits.
Figure 2:
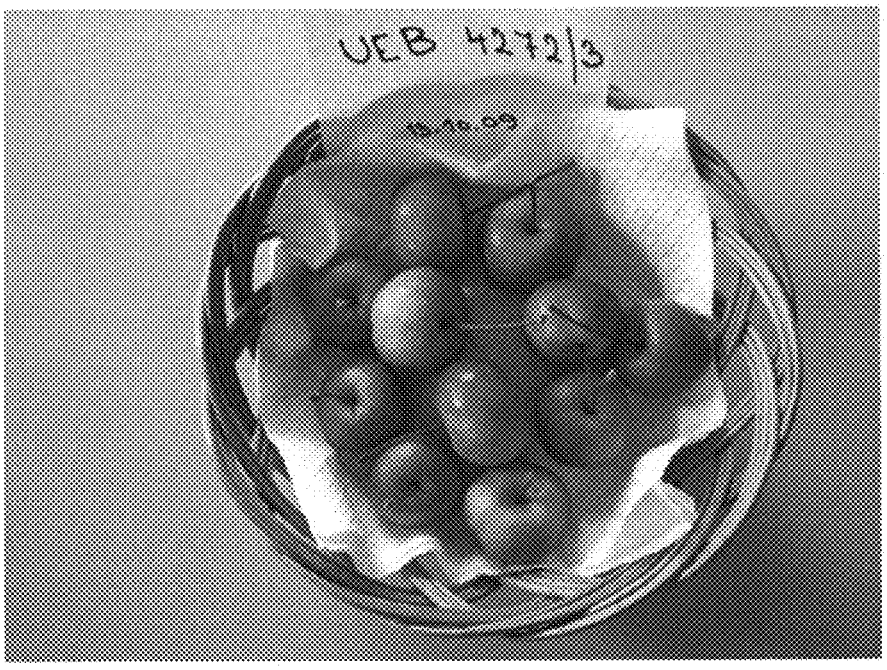
FIG. 2 illustrates details of fruits of the new variety from a 5-year old tree.
Figure 3:
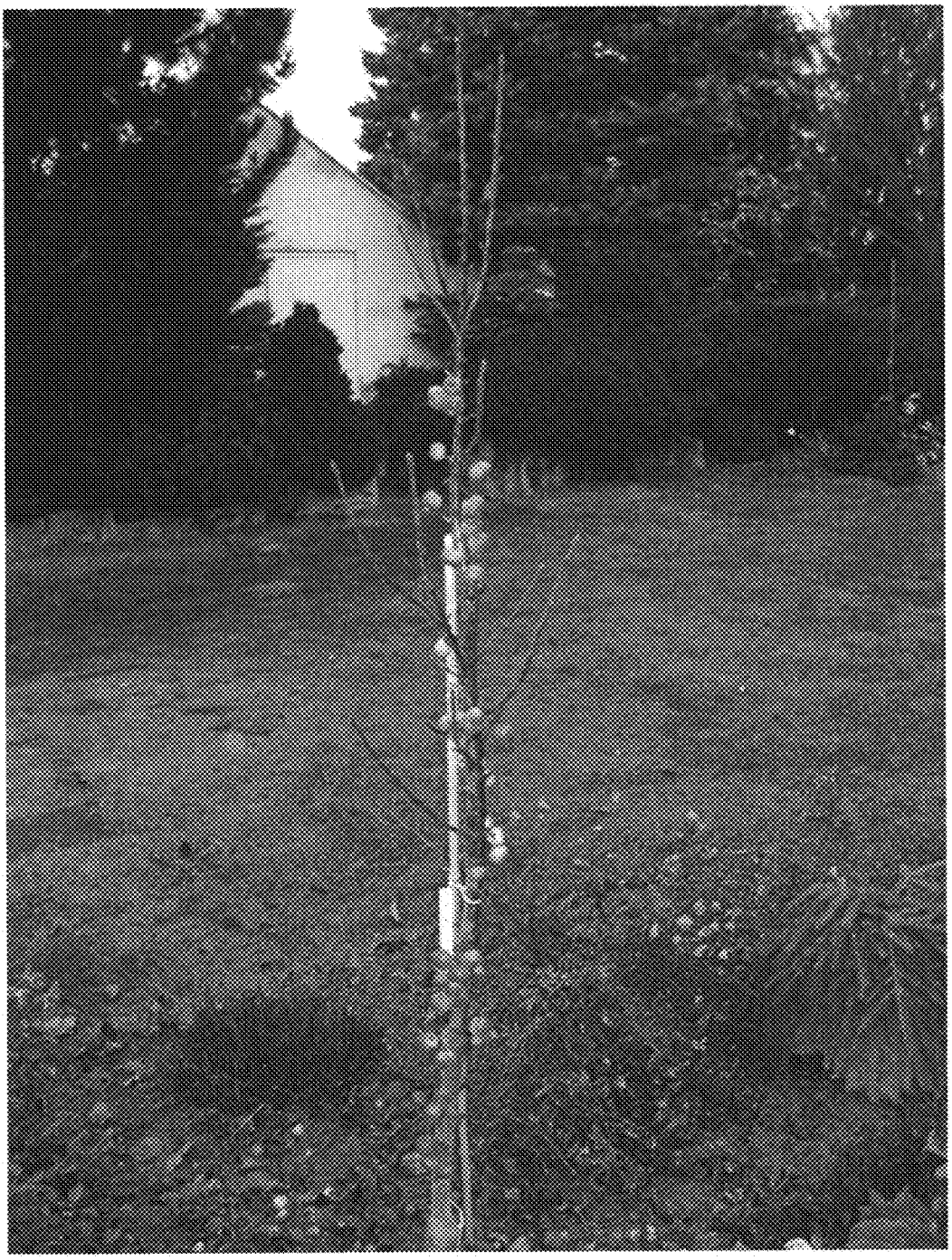
FIG. 3 illustrates a young tree of the new variety grafted on MM 106 rootstock at 2 years of age, demonstrating that the fruits are persistent on the tree after its leaves fall into Winter.
Figure 4:
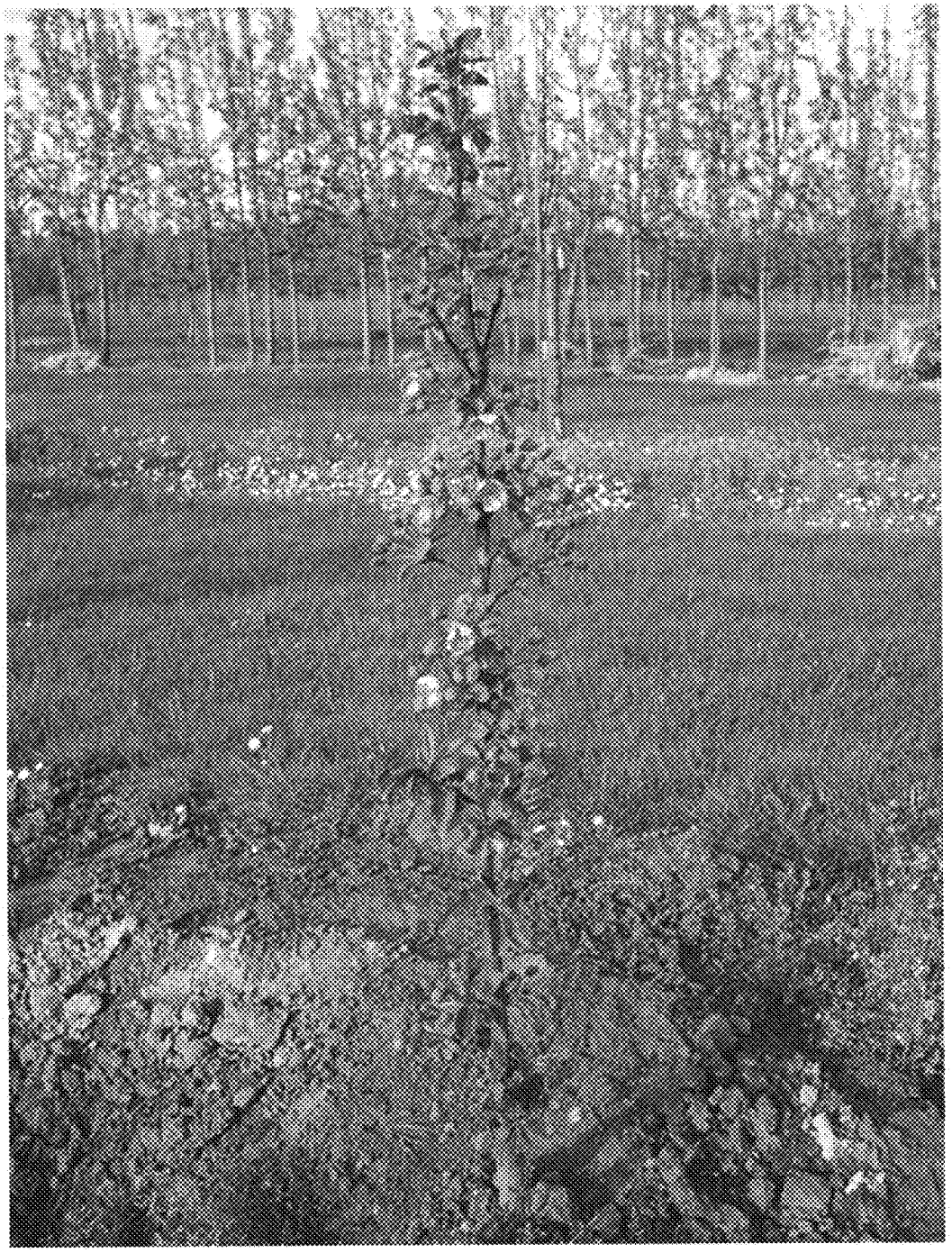
FIG. 4 illustrates a young tree of the new variety grafted on MM 106 rootstock at 2 years of age, at first flower opening.
Figure 5:
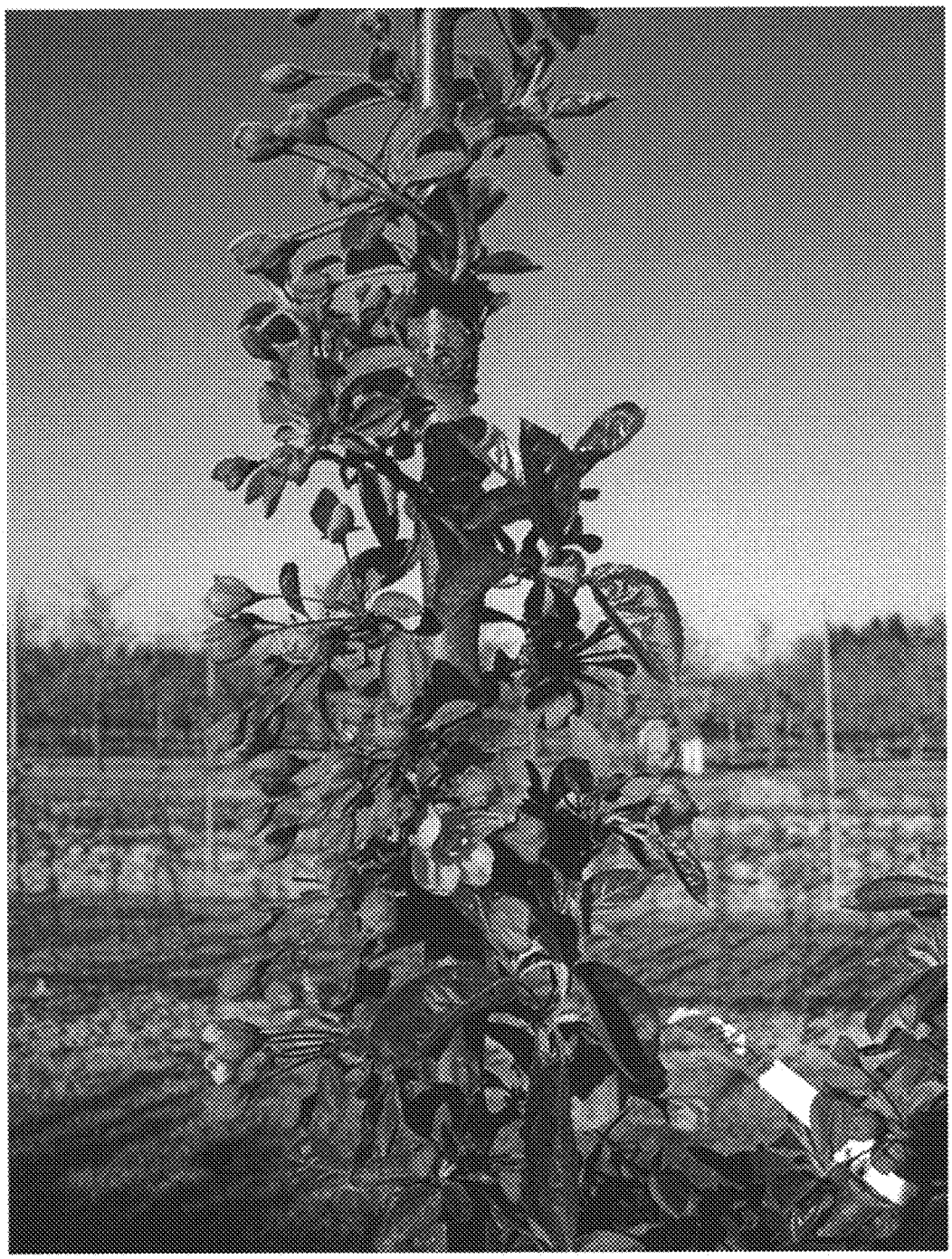
FIG. 5 illustrates a section of the vertical trunk of the new variety at 3 years of age, showing predominantly unopened flowers at the beginning of blossoming time.
Figure 6:
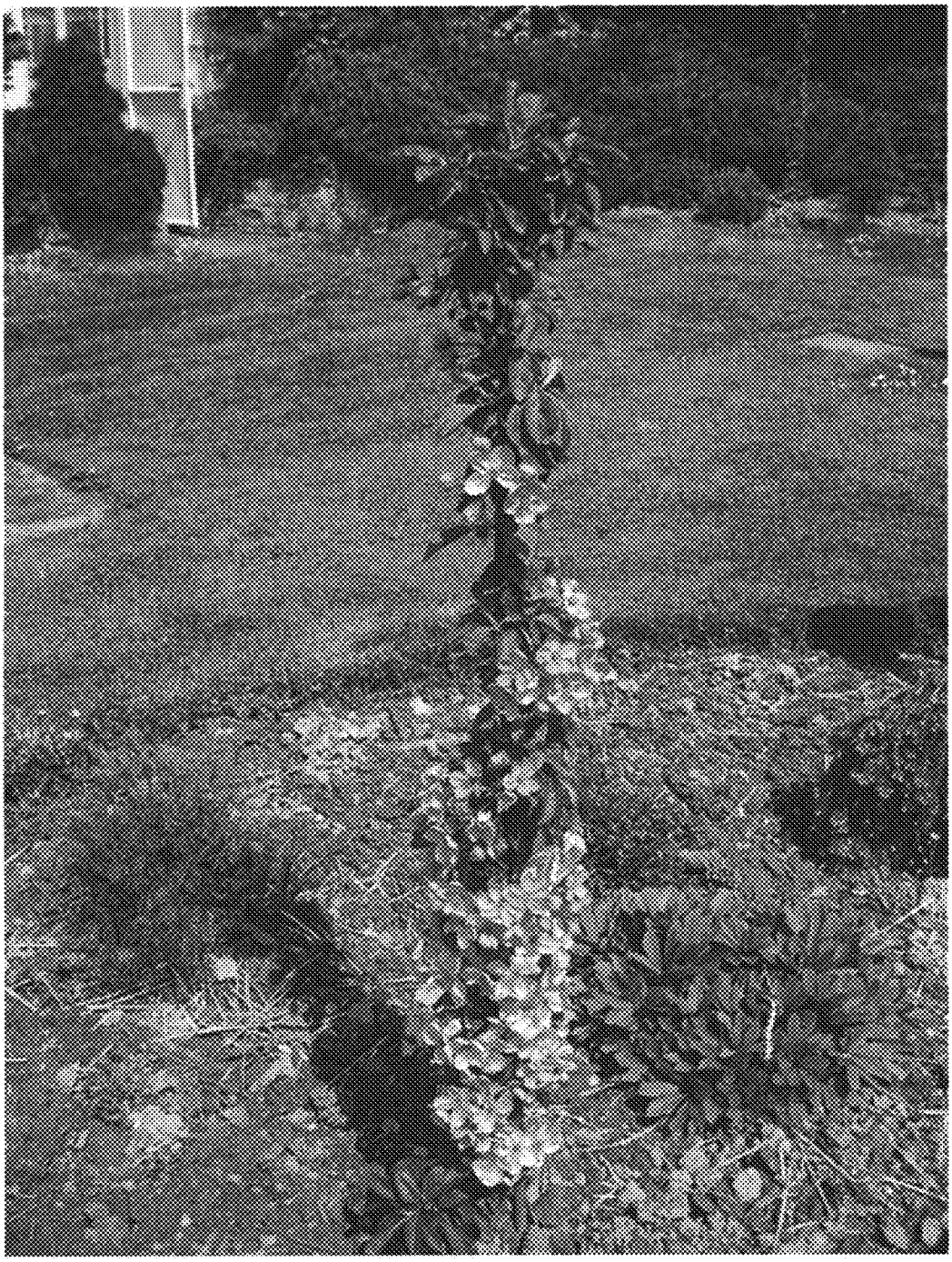
FIG. 6 illustrates a young tree of the new variety grafted on MM 106 rootstock at 5 years of age, with fully opened flowers.
Figure 7:
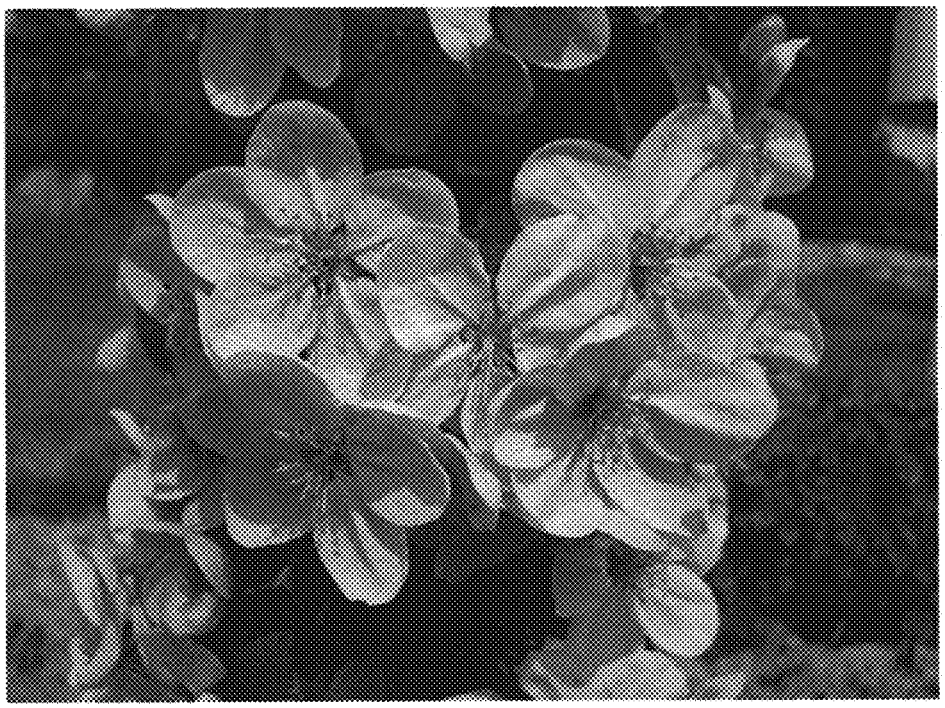
FIG. 7 illustrates details of fully opened flowers of the new variety from a 5-year old tree.
Figure 8:
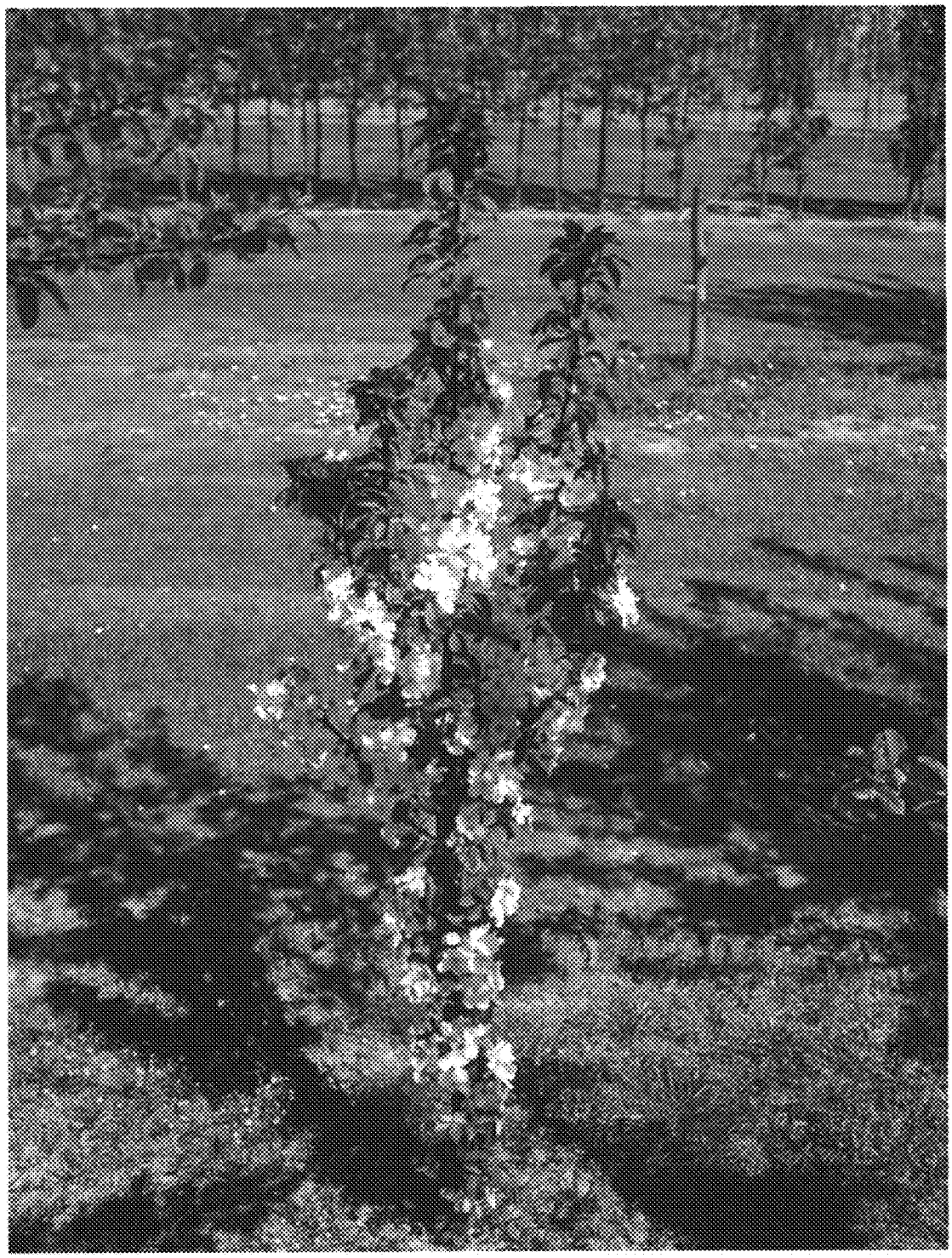
FIG. 8 illustrates a young tree of the new variety grafted on MM 106 rootstock at 5 years of age, at the end of blossoming time.
Figure 9:
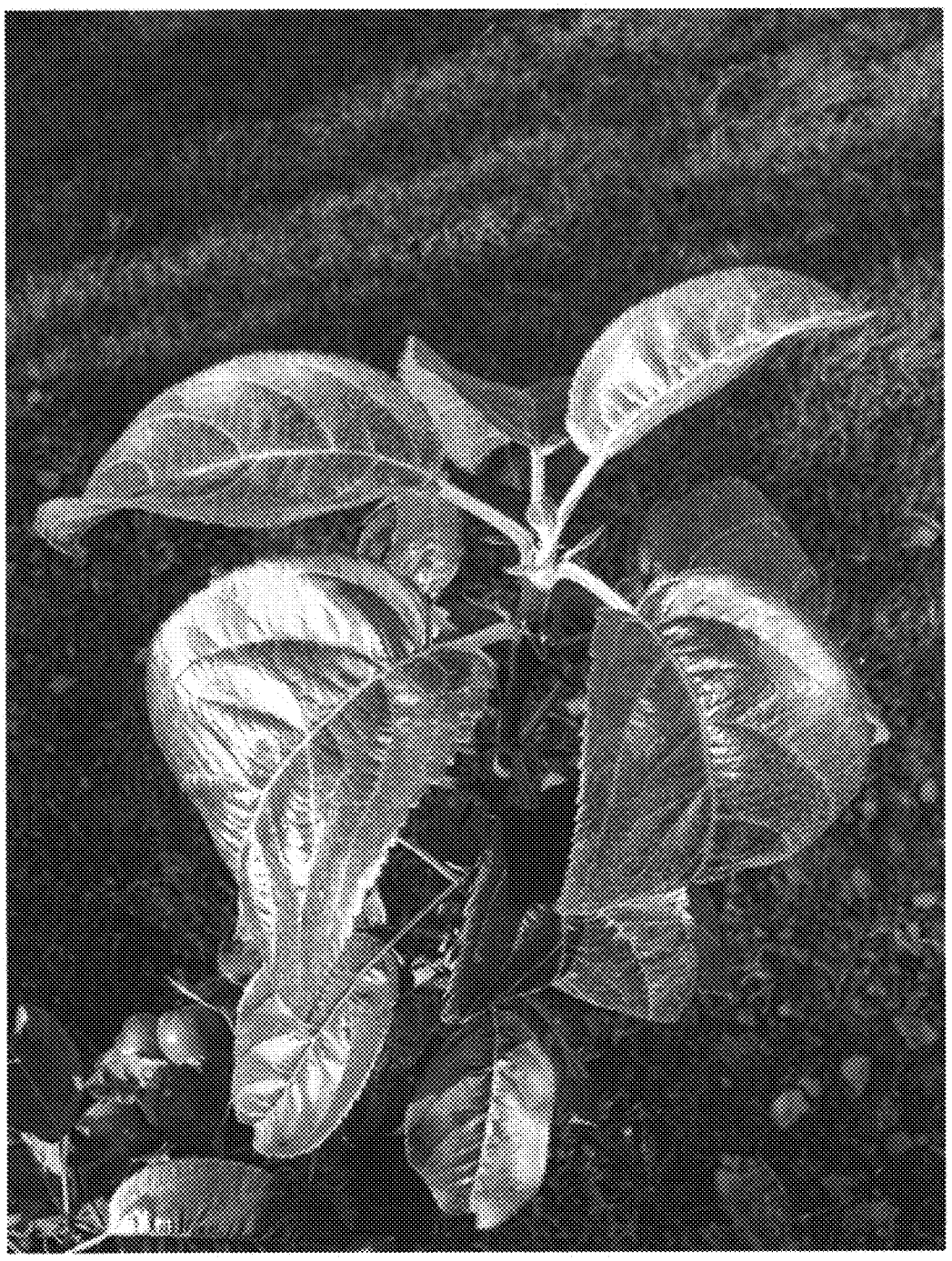
FIG. 9 illustrates a growing shoot of the new variety from a 5-year old tree.
Figure 10:
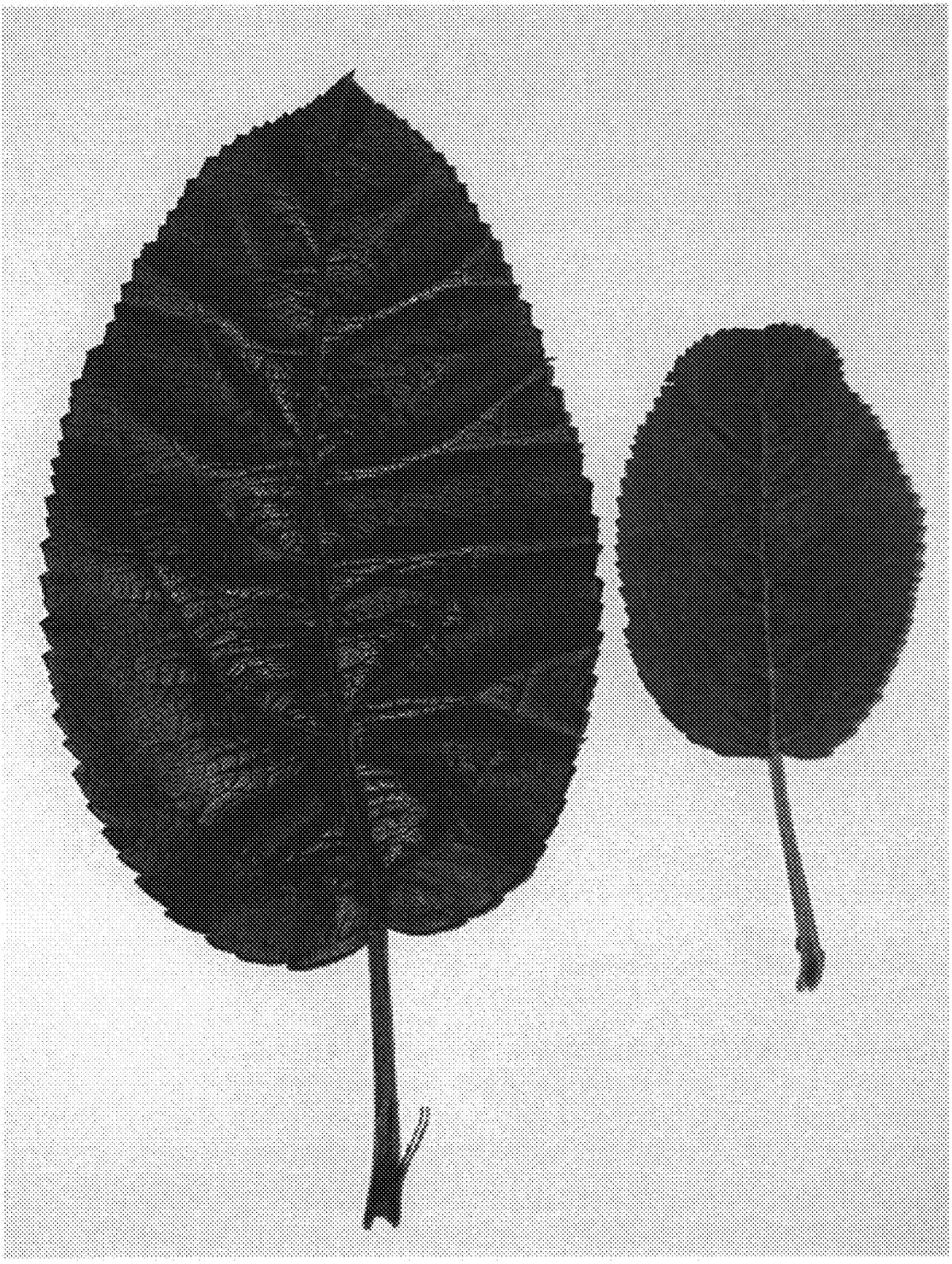
FIG. 10 illustrates a close-up view of a mature leaf and a young leaf of the new variety from a 4-year old tree.

The following detailed description sets forth characteristics of the new cultivar. The new variety was grown under natural field conditions in The Czech Republic. The following fertilizer combination was used (Kg/ha/year): 55 parts nitrogen, 25 parts phosphorous, 60 parts potassium, 55 parts calcium, and 5 parts magnesium. Color references are primarily to The 1986 R.H.S. Colour Chart of The Royal Horticultural Society of London (in association with the Flower Council of Holland), Second Edition, and were identified under natural light.

Tree:

*Age*.—Approximately 3 years.

*Size*.—Crown height of 1.6 m, width of 0.25 m.

*Vigor*.—Medium.

*Density*.—High.

*Form*.—Erect and compact.

*Production*.—Very precocious.

*Growth type*.—Columnar.

*Bearing*.—Annual; predominantly on spurs.

*Average productivity*.—4.5 kg per 5-year old tree.

Trunk:

*Size*.—Approximately 4.0 cm in diameter at 30.0 cm from the soil line.

*Surface texture*.—Smooth.

*Bark color*.—Greyed-Orange Group RHS 166A.

*Lenticels* (50.0 *cm above ground*).—Length: 1.0 mm to 2.0 mm. Width: 0.5 mm to 1.0 mm. Color: Greyed-Orange Group RHS 164C. Density: Variable, with 5 to 7 lenticels on average per 1 $cm^2$.

Branches: Not applicable—absent. The variety lacks a conventional branching system along the tree trunk.

Leaves:

*Length*.—About 60.0 mm to about 86.0 mm, averaging 69.0 mm.

*Width*.—About 38.0 mm to about 51.0 mm, averaging about 45.0 mm.

*Form*.—Ovate.

*Texture*.—Smooth.

*Thickness*.—Thin.

*Base*.—Rounded and asymmetric.

*Apex*.—Acuminate.

*Margin*.—Serrate.

*Attitude of leaf blade in relation to the shoot*.—Downwards.

*Pubescence*.—Upper surface: None present. Lower surface: Very fine.

*Color*.—Young leaves: Upper surface: Greyed-Purple Group RHS 183A. Lower surface: Greyed-Purple Group RHS 183D. Mature leaves: Upper surface: Green Group RHS 139A, combined with some Greyed-Purple Group RHS 187A. Lower surface: Green Group RHS 137C, combined with some Greyed-Purple Group RHS 185C.

*Stipule*.—Length: 0.6 cm. Shape: Narrow and elongated, with an acute apex. Color: Greyed-Purple Group RHS 183B.

*Petiole*.—Shape: Straight, with thickening and flattening at the base. Length: About 27.0 mm to 38.0 mm, averaging about 32.0 mm. Diameter: About 1.0 mm in the middle. Color: Red-Purple Group RHS 59A to 59B.

*Veins*.—Description: Palmate, medium dense, with pinnate main veins and netted minor veins. Color: Upper surface: Greyed-Purple Group RHS 186A. Lower surface: Greyed-Purple Group RHS 187A to 187B.

Flower buds:

*Pedicel*.—Length: Typically in the range of 26.0 mm to 38.0 mm, with an average of 32.0 mm. Diameter: 1.1 mm on average. Color: Predominantly Red-Purple Group RHS 59A.

*Bud*.—Length: 14.0 mm on average. Width: 10.0 mm on average. Color: Predominantly Red-Purple Group RHS 59B to 59C.

Flowers:

*Bloom timing*.—At the end of April/1$^{st}$ of May — three days before 'Golden Delicious'.

*Pollination requirements*.—Self-sterile, needs pollinators such as *Malus* x *zumi* (crab apple) 'Professor Sprenger' (unpatented).

*Number of flowers per cluster*.—5 to 7.

*Fragrance*.—Faint.

*Average diameter*.—4.3 cm.

*Petals*.—Number: 5. Length: From 22.0 mm to 28.0 mm, with an average of 25.0 mm. Width: From 20.0 mm to 24.0 mm, with an average of 21.0 mm. Shape: Round to slightly oval. Apex: Obtuse. Base: Mucronate. Aspect: Positioned overlapping. Margin: Entire. Texture and appearance: Soft and smooth. Color: When opening: Upper surface: Red-Purple Group RHS 63B. Lower surface: Red-Purple Group RHS 63B to 63C. Fully opened: Upper surface: Red-Purple Group RHS 62B. Lower surface: Red-Purple Group RHS 62C.

*Sepals*.—Number: 5 (average). Shape: Long-conical; pointed. Margin: Entire. Texture: Finely pubescent (colorless). Length: Average of 7.0 mm from the union. Width: 3.0 mm in the middle. Color: Upper surface: Yellow-Green Group RHS 144B, with a Red-Purple Group RHS 59A apex. Lower surface: Red-Purple Group RHS 59B, with a with a Red-Purple Group RHS 59A apex.

*Stamens*.—Number (per flower): Average of 19. Filament length: 6.0 mm to 9.0 mm.

*Anthers*.—Shape: Oval. Length: 2.0 mm. Color: Yellow Group RHS 10C.

*Pollen*.—Color: Yellow Group RHS 10B. Amount (generally): Medium to high.

*Pistils*.—Length: 12.0 mm on average.

*Style*.—Length: 9.0 mm on average. Color: Red Group RHS 51C.

*Stigma*.—Shape: Rounded. Color: Red Group RHS 38A.

Fruit:

*Bearing*.—Predominantly on spurs.

*Maturity when described*.—Harvest maturity (date of picking).

*Date of picking*.—Oct. 30, 2018.

*Size*.—Axial diameter: 22.0 mm to 29.0 mm; averaging about 25.0 mm. Transverse diameter: 32.0 mm to 37.0 mm; averaging about 33.0 mm.

*Weight per fruit*.—Average of 12 g.

*Form*.—Obloid; generally slightly ribbed and rarely medium ribbed.

*Cavity*.—Shape: Funnel. Depth: 4.0 mm-5.0 mm on average. Breadth: 10.0 mm-12.0 mm on average.

*Basin*.—Shape: Bowl. Depth: 7.0 mm-8.0 mm on average. Width: 15.0 mm on average.

*Calyx*.—Variable, but about 60% of fruits have no calyx lobes and about 40% exhibit a persistent calyx with semi-erect lobes.

Skin:

*Thickness*.—Medium.

*Texture*.—Smooth, free of russet, with bloom on skin present.

*Tendency to crack*.—Absent.

*Overcolor*.—Red Group RHS 46A to 44A, 40-80% presence with bloom on the fruit Red-Purple Group RHS 58A.

*Ground color*.—Yellow-Green Group RHS 153A to Greyed-Yellow Group RHS 160A.

*Young fruit anthocyanin coloration*.—100% presence with very dark and high intensity.

*Lenticels*.—Average number of fruit: 238. Average length: 0.39 mm. Average width: 0.34 mm. Color: Orange-White Group RHS 159B to 159C.

Flesh:

*Aroma*.—Weak, like an ornamental apple.

*Color*.—Red Group RHS 45A to Orange-White Group RHS 159A.

*Texture*.—Fine, firm.

*Eating quality*.—Not applicable, an ornamental variety.

Core:

*Bundle area*.—Obloid on longitudinal section.

*Aperture of the locules in the transverse section*.—Moderately open.

*Bundle*.—Vascular strands are weakly distinguishable.

*Calyx tube*.—Short.

*Depth of tube to shoulder*.—3.5 mm on average.

*Styles*.—Often absent, rarely persistent as dry residues.

*Stamens*.—Often absent, rarely persistent as dry residues.

*Seed cells*.—Wall: Smooth. Depth: 4.0 mm to 5.0 mm on average. Breadth: 5.0 mm on average. Longitudinal section: 6.0 mm on average.

Seeds:

*Number perfect*.—8 to 12 seeds, averaging about 10.

*Number in one cell*.—Mainly 2, sometimes 1 seed present.

*Length*.—7.0 mm on average.

*Breadth*.—4.0 mm on average.

*Form*.—Flattened and pyramidal with an acute tip.

*Color*.—Greyed-Orange Group RHS 175A to Greyed-Purple Group RHS 183A.

Stem:

*Length*.—22.0 mm to 37.0 mm, averaging 28.5 mm.

*Width*.—0.9 mm to 1.4 mm, averaging 1.1 mm.

*Color*.—Greyed-Purple Group RHS 187A at the top to 187C at the base.

General:

*Use*.—As an ornamental variety having a columnar tree growth type.

*Shipping quality*.—Not applicable — ornamental variety.

*Keeping quality*.—Not applicable — ornamental variety.

*Tree winter hardiness*.—No frost damage observed at the place of origin, lowest winter temperatures approximately −20° C.

*Bud winter hardiness*.—No frost damage observed at the place of origin, lowest winter temperatures approximately −20° C.

*Drought tolerance*.—Unknown.

*Disease resistance*.—$V_f$-resistance against scab.

We claim:

1. A new and distinct variety of *Malus domestica* (Borkh.) apple tree plant substantially as is herein described and illustrated.

* * * * *